(12) United States Patent
Thiebaut et al.

(10) Patent No.: US 7,009,070 B2
(45) Date of Patent: Mar. 7, 2006

(54) MODIFICATION OF THE CATALYTIC SYSTEM IN AN INDUSTRIAL PROCESS FOR MAKING ACETIC AND/OR METHYL ACETATE ACID

(75) Inventors: Daniel Thiebaut, Lescar (FR); Daniel Marchand, Jurancon (FR); Philippe Kalck, Auzeville Tolosane (FR); Carole Le Berre, La Croix Falgarde (FR); Philippe Serp, Toulouse (FR)

(73) Assignee: Acetex Chimie, Neuilly sur Seine Cedex (FR)

( * ) Notice: Subject to any disclaimer, the term of this patent is extended or adjusted under 35 U.S.C. 154(b) by 99 days.

(21) Appl. No.: 10/433,474

(22) PCT Filed: Feb. 5, 2002

(86) PCT No.: PCT/FR02/00432

§ 371 (c)(1),
(2), (4) Date: Jun. 11, 2003

(87) PCT Pub. No.: WO02/062739

PCT Pub. Date: Aug. 15, 2002

(65) Prior Publication Data

US 2004/0044245 A1 Mar. 4, 2004

(30) Foreign Application Priority Data

Feb. 8, 2001 (FR) .................................. 01 01690

(51) Int. Cl.
*C07C 67/36* (2006.01)
*C07C 53/08* (2006.01)
(52) U.S. Cl. ............... 560/232; 560/231; 562/607; 562/519
(58) Field of Classification Search ............ 562/512, 562/517, 518, 519, 500; 560/129, 232, 438, 560/292
See application file for complete search history.

(56) References Cited

U.S. PATENT DOCUMENTS

| 5,625,094 A | 4/1997 | Nobel et al. |
| 5,939,585 A * | 8/1999 | Ditzel et al. ................. 562/519 |

FOREIGN PATENT DOCUMENTS

| GB | 2315069 | 1/1998 |
| WO | WO00/27785 | * 5/2000 |

* cited by examiner

*Primary Examiner*—Johann Richter
*Assistant Examiner*—Karl Puttlitz

(74) *Attorney, Agent, or Firm*—Dennison, Schultz, Dougherty & MacDonald

(57) ABSTRACT

The invention relates to a continuous process for the manufacture of acetic acid and/or methyl acetate, characterized in that, during the continuous operation of the installation for a continuous industrial process, called the initial process, for the carbonylation of methanol or a carbonylatable derivative of methanol such as dimethyl ether, methyl halides or methyl acetate, in the homogeneous liquid phase and under carbon monoxide pressure, in the presence of a catalyst system comprising a rhodium-based homogeneous catalyst and a halogenated promoter, and in the presence of a concentration of water greater than or equal to 14% in the reaction medium, the composition of said homogeneous catalyst is modified gradually by adding an iridium compound over time.

This process makes it possible on the one hand to modify the composition of the catalyst system so as to change from a homogeneous catalyst based on rhodium alone to a catalyst based on rhodium and iridium, or even iridium alone, without stopping the installation, and on the other hand to reduce the water content of the reaction medium once the iridium additions have been effected.

18 Claims, No Drawings ns of the catalyst system is modified in a particularly smooth and uniform manner, making it possible, in said industrial process, to change from a catalyst system based on rhodium alone to a catalyst system based on rhodium, and iridium, or even based on iridium alone, without having to shutdown the production unit in order to effect this change of catalyst.

MODIFICATION OF THE CATALYTIC SYSTEM IN AN INDUSTRIAL PROCESS FOR MAKING ACETIC AND/OR METHYL ACETATE ACID

BACKGROUND OF THE INVENTION

The present invention relates to the field of the industrial manufacture of acetic acid and/or methyl acetate.

It relates more particularly to a continuous process for the manufacture of acetic acid and/or methyl acetate during which the composition of the catalyst system is modified in a particularly smooth and uniform manner, making it possible, in said industrial process, to change from a catalyst system based on rhodium alone to a catalyst system based on rhodium, and iridium, or even based on iridium alone, without having to shutdown the production unit in order to effect this change of catalyst.

Numerous industrial processes are known for the manufacture of acetic acid and/or methyl acetate in the liquid phase under pressure using a homogeneous catalyst system.

The invention applies quite specifically to the modification of processes which initially involve the carbonylation of methanol or a carbonylatable derivative of methanol in the presence of a rhodium-based catalyst.

The patents of Paulik et al., which form the basis of the so-called "Monsanto" technology or process, describe the carbonylation of reactants in the liquid or vapor phase by homogeneous or heterogeneous catalysis with rhodium (U.S. Pat. No. 3,769,329) or iridium (U.S. Pat. No. 3,772,380). In this technology the reactants consist of alcohols ROH, ethers R'—O—R', esters R'C(O)OR' and halides R—X in which the total number of carbons is less than or equal to 20. The carbonylation reaction is carried out in the presence of one of these reactants, carbon monoxide (CO partial pressure of between 1 and 15,000 psig), a catalyst system comprising rhodium or iridium in the presence of a halogenated promoter, and water, at a temperature of between 50 and 300° C.

The first carbonylation processes to be developed were catalyzed by a rhodium compound in the presence of a methyl halide, preferably methyl iodide, as co-catalyst. These processes were regularly improved to increase the reaction rates (and hence the productivity of the process), decrease the production of impurities, increase the stability of the catalyst in solution and reduce the manufacturing costs.

In particular, it has been possible to reduce the water content by adding large amounts of iodide ions to the reaction medium (more than 0.3 mol/liter in patent FR 2 551 434) and/or by maintaining imposed concentrations of the constituents of said reaction medium (EP 0 161 874 and EP 0 250 189).

Recently, studies performed with a view to replacing rhodium with iridium have culminated in novel so-called "low water content" processes catalyzed by iridium alone (EP 0 618 184, EP 0 616 997, EP 0 786 447) or by iridium in the presence of co-promoters, mainly ruthenium, osmium or rhenium (EP 0 643 034, EP 0 728 729,EP 0 752 406).

Conventionally, these various processes of carbonylation in the liquid phase under homogeneous catalysis are carried out in an installation comprising 3 separate zones. In the 1st zone, called the reaction zone, methanol or a carbonylatable derivative of methanol is carbonylated with carbon monoxide under pressure by simultaneous introduction of the 2 reactants. A given composition of the reaction medium is maintained by introducing the above two reactants and recycling streams originating from the 2nd and 3rd zones downstream. In the 2nd zone, called the vaporization zone or flash zone, the reaction medium is partially vaporized at a pressure below that in the 1st reaction zone, the expansion being effected with or without the provision of heat. The vaporized fraction, consisting mainly of the unreacted reactants, water, methyl iodide, methyl acetate and acetic acid, is transferred to the 3rd zone, called the zone for distillative separation and purification of the acetic acid and/or methyl acetate produced. The non-vaporized fraction coming from the 2nd flash zone, which is composed essentially of acetic acid and catalyst, is recycled into the 1st reaction zone. The 3rd zone, which conventionally consists of 3 distillation columns, makes it possible to separate the different components, to recycle those necessary for carrying out the reaction, and to produce purified acetic acid and/or methyl acetate. These processes also comprise a section for treatment of the gases and/or vents. For further details, reference may be made to the article by M. J. Howard et al., CATALYSIS TODAY, 18 (1993) 325–354.

Even more recently, carbonylation processes have been described which employ catalyst systems composed of both rhodium and iridium.

Patent EP 0 618 183, relating to the carbonylation of alcohols or derivatives, shows the synergism of a catalyst system composed of both rhodium and iridium compared with systems consisting of rhodium or iridium as the only metal. This process is carried out in the presence of small concentrations (0 to 5%, preferably 0 to 2%) of a catalyst stabilizer such as a soluble iodide salt, or in the absence of such compounds.

The soluble iodide salts consist of alkali metal or alkaline earth metal iodides or quaternary ammonium or phosphonium iodides.

Patent FR 2 750 984 describes the improvement in carbon monoxide consumption brought about by introducing a 2nd carbonylation reactor between the 1st zone (main reactor) and the 2nd vaporization (flash) zone; the catalyst system is composed of iridium, optionally in combination with rhodium.

Patent FR 2 750 985 relates to the carbonylation of methanol and proposes a method of stabilizing the catalyst system composed of soluble iridium and rhodium complexes, said method consisting in maintaining a water concentration of more than 0.5% in the non-vaporized liquid fraction recycled from the 2nd vaporization (flash) zone into the 1st reaction zone.

International patent application WO 00/27785 shows the synergism of a catalyst system composed of iridium and platinum, and optionally rhodium, compared with systems consisting of only one metal. Said patent application recommends maintaining a molar ratio of less than 10 between the soluble iodide salts introduced and the iridium.

International patent application WO 00/78700 relates to the production of acetic acid by means of simultaneous reactions involving the isomerization of methyl formate and the carbonylation of methanol in the presence of iridium and optionally rhodium. Said patent application teaches the stabilization of the catalyst system by maintaining the concentration of formyl radicals (methyl formate+formic acid) above 1% in the non-vaporized fraction from the 2nd vaporization (flash) zone. It is recommended to keep iodides in the soluble ionic form in this medium, although their concentration range is not stated.

International patent application WO 00/24701 describes the carbonylation of methanol with a catalyst system composed of both rhodium and iridium, in the presence of iodide ions as stabilizers/co-promoters of these catalysts. The composition of the reaction medium is kept constant: water <14% (preferably 0.1 to 8%), methyl iodide 5 to 30%, methyl acetate 0.5 to 30%, iodides (preferably lithium iodide) 2 to 20% and catalysts 100 to 5000 ppm for each metal; the catalyst system can also comprise a salt of a transition metal, preferably ruthenium.

The above patents and patent applications describe carbonylation reaction media established on the basis of a catalyst system which is composed of both rhodium and iridium and whose composition has been optimized to achieve the results expected of these inventions. None of these documents either indicates or suggests changing from a catalyst system composed of rhodium alone to a catalyst system based on a mixture of rhodium+iridium catalysts.

Furthermore, in such a change, it is well known that attention must be paid to the role of the corrosion metals commonly and conventionally present in carbonylation reaction media (iron, nickel, chromium, molybdenum, tungsten, zirconium and any metals which originate from the corrosion of industrial equipment and can be recycled into the reactor during production). As is apparent in particular in patent FR 2 551 434, these corrosion metals are generally considered overall to have detrimental effect in catalysis by rhodium alone, since they accelerate the conversion reaction or water gas reaction (also abbreviated to WGSR for Water Gas Shift Reaction):

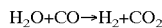

$$H_2O + CO \rightarrow H_2 + CO_2$$

Again in catalysis by rhodium alone, patent EP 0 384 652, which is more selective, recommends removing iron and nickel in order to leave only the group VIb metals (Mo, W, Cr), which have a positive influence on the carbonylation rate and hence the productivity of the process. A variant consists in adding these group VIb corrosion metals to the carbonylation reaction medium.

On the other hand, in catalysis by iridium alone, the problem presented by the corrosion metals seems to be simpler: their concentration in the reaction medium must be limited to a few hundred ppm (patent FR 2 750 984) or to a value below 200 ppm (patent applications WO 00/27785 and WO 00/78700) in order to limit:

firstly the water gas reaction, as in the case of rhodium, and secondly the concentration of iodide ions, which are considered to poison carbonylation catalyzed by iridium. In fact, these iodide ions, which originate from different sources, are introduced in part by the salts represented by the iodides of the corrosion metals. Patent FR 2 750 984 and patent application WO 00/27785 propose that the molar ratio of the iodide ions to the iridium be kept below 10.

As can be seen from the foregoing, in view of the different influence (depending on the catalyst system) of both the concentration of corrosion metals and the concentration of iodide ions in the case of continuous processes for the manufacture of acetic acid by the carbonylation of methanol or one of its carbonylatable derivatives, the only solution hitherto envisaged by those skilled in the art wishing to change from a catalyst system based on rhodium to a catalyst system based on rhodium considerably enriched in iridium, or based on iridium alone, is to stop the installation in order to modify the reaction medium, in particular so as to adjust the concentration of corrosion metals and iodides to values which do not disturb the satisfactory running of the process with the new catalyst system.

SUMMARY OF THE INVENTION

Now, contrary to all expectations, the inventors of the present invention have shown that it is possible, without stopping the installation, to modify the composition of the catalyst by uniformly and progressively adding an iridium-based catalyst to a carbonylation reaction medium originally catalyzed by a rhodium-based catalyst and having the conventional composition known from the Monsanto technology, i.e. a reaction medium containing at least 14% of water, at most 15% of methyl iodide, at most 2% of methyl acetate and a few hundred ppm of rhodium, in the presence of a few thousand ppm of corrosion metals, the remainder consisting of acetic acid.

The present invention therefore proposes to modify the catalyst system in a conventional industrial process for the manufacture of acetic acid, or Monsanto-type process, catalyzed by rhodium, by at least partial replacement of the rhodium with iridium:

without stopping the process to effect the change from the catalyst system comprising rhodium alone to the system comprising rhodium+iridium, without profoundly modifying the composition of the reaction medium, particularly the iodide ions naturally present and the corrosion metals, without detracting from the stability of the catalyst system, while maintaining or improving the carbonylation rate and hence the productivity of the process, and while reducing the manufacturing costs by decreasing the water content of the reaction medium to afford an energy saving in the distillations.

However, other advantages will become more clearly apparent from the detailed description which follows.

DETAILED DESCRIPTION OF THE INVENTION

It has become apparent in particular that the catalyst system can be modified in a particularly smooth manner and without stopping the installation; this represents a first economic advantage since it makes it possible to avoid completely stopping the installation in order to modify the reaction medium. It has also become apparent that it is possible, in the course of this modification of the catalyst system aimed at enriching it in iridium, to decrease the water content considerably; this constitutes a second considerable economic advantage of the process of the invention. Furthermore, this modification of the water content of the reaction medium makes it possible, under industrial conditions, to envisage carrying out a methyl formate isomerization reaction simultaneously with the initial carbonylation, said isomerization reaction also leading to the formation of acetic acid and/or methyl acetate, or even to limit the production of acetic acid and/or methyl acetate to the methyl formate isomerization reaction alone; all these modifications are effected without stopping the installation, which represents a considerable economic advantage.

Thus, according to one of its essential characteristics, the invention relates to a continuous process for the manufacture of acetic acid and/or methyl acetate, characterized in that, during the continuous operation of the installation for a continuous industrial process, called the initial process, for the carbonylation of methanol or a carbonylatable derivative of methanol such as dimethyl ether, methyl halides or methyl acetate, in the homogeneous liquid phase and under carbon monoxide pressure, in the presence of a catalyst system comprising a rhodium-based homogeneous catalyst and a halogenated promoter, and in the presence of a concentration of water greater than or equal to 14% in the reaction medium, the composition of said homogeneous catalyst is modified gradually by adding an iridium compound over time.

The process of the invention therefore consists in gradually modifying, over time, the composition of the catalyst system used in a manufacturing process, called the initial process, which is derived from the Monsanto process, i.e. a process in which acetic acid and/or methyl acetate are manufactured continuously by the carbonylation of methanol or a carbonylatable derivative of methanol in the liquid phase under pressure, in the presence of a homogeneous catalyst containing rhodium.

The process of the invention therefore comprises an essential step, hereafter referred to as the modification phase, during which the catalyst system is modified by adding an iridium-based compound without stopping the production, i.e. without stopping the installation, without having to empty it and without having to wash, clean or condition it in any way in order to effect the change of catalyst system.

The process of the invention, as described above, applies to any initial process derived from the Monsanto process which initially operates with a catalyst system comprising a rhodium-based homogeneous catalyst and a halogenated promoter, the latter being methyl iodide in particular.

Like any system of the Monsanto type, this starting system operates with a reaction medium having a water content greater than or equal to 14%.

The modification phase of the process according to the invention can extend over periods which may vary according to the composition of the target catalyst system, and on average will extend over a period of a few months to about 5 years.

The end of the modification phase of the process of the invention makes it possible to change from a system catalyzed by rhodium alone to a system catalyzed by a homogeneous catalyst based on a mixture of rhodium and iridium, or a system catalyzed by iridium alone.

The end of the modification phase of the process will easily be determined by those skilled in the art, both on the basis of preliminary experiments of the type performed in the "Examples" section of the present document, and also on the basis of the results obtained during the modification phase, with a view to improving both the productivity and the kinetics of the process for the manufacture of acetic acid and/or methyl acetate.

Thus, after this modification phase, the continuous manufacture of acetic acid and/or methyl acetate can be continued while maintaining the composition of the catalyst system as modified in the modification phase. This new phase will hereafter be referred to as the stabilization phase.

In this phase following the modification phase, the concentrations of rhodium and iridium in the reaction medium are maintained by adding rhodium compounds and/or iridium compounds in order to compensate, in the manner conventional in the art, the losses of catalyst during the continuous manufacturing operations and particularly losses due to possible entrainments of the catalyst, which are difficult to avoid despite the various recycling operations performed in an industrial process.

It is common and conventional, in a carbonylation process catalyzed by rhodium alone (or iridium alone), to maintain or adjust the catalytic activity in the reaction zone by adding rhodium (or iridium) with greater or lesser frequency. These additions are intended e.g. to keep the concentration of active catalyst constant in the reaction medium in order to compensate the losses of catalyst due to insolubilization (inactive catalyst) or due to vesicular entrainment in the vaporization and distillation operations conventionally carried out in flash and distillation/purification zones.

In the case of the present invention, the various additions of iridium compounds during the modification phase can be effected in different ways, particularly in a uniform or non-uniform manner and continuously or batchwise, but always without stopping the production.

In one variant of the invention, the additions are effected in the form of presolubilized iridium and particularly in the form of iridium solubilized in any solution compatible with the reaction medium. This variant is particularly advantageous because it is very easy to carry out on an industrial scale. The solution can be prepared from solid compounds conventionally used in processes catalyzed by iridium (metal, oxides or hydroxides, complex salts, etc.). This solubilization can be effected by any of the means known to those skilled in the art and consistent with the rules of the art, and particularly by using processes such as those described in patents EP 0 657 386 and EP 0 737 103, which describe the means of preparing directly injectable catalyst solutions useful in carbonylation reactions.

Preference will generally be given to iridium solubilization procedures which are compatible with industrial installations used for solubilizing rhodium in conventional carbonylation processes.

In another variant, the iridium compound can be introduced in the form of a solid iridium derivative which is solubilized in situ in the reaction medium.

In such a case, the iridium derivative is introduced directly into the reactor and its solubilization and the synthesis of the catalytically active species take place in the reaction medium in the presence of a halogenated promoter, particularly methyl iodide, and under carbon monoxide pressure.

Thus, in all cases, the result is a carbonylation reaction catalyzed by a mixture of rhodium and iridium whose concentrations in the reaction medium can be adjusted at any moment by adding rhodium or iridium or both at once.

As explained previously, the iridium compound can thus be introduced into the reaction medium in different physical forms.

The introduction can also be performed according to different variants.

In a first variant, the more or less frequent additions of rhodium effected in the initial process are simply replaced with corresponding additions of iridium throughout the modification phase.

Therefore, in this variant, iridium compounds are added so as to compensate the losses of rhodium, the lost rhodium being replaced with iridium.

In another variant, the iridium compound is added continuously.

In yet another variant, the iridium is added batchwise.

In all cases, as explained previously, the preliminary experiments and the monitoring of both the reaction kinetics and the productivity of the system will make it possible to determine when the modification phase stops and changes to the stabilization phase in which the catalyst system is stabilized at the determined Ir/Rh molar ratio.

In the different variants for introduction of the iridium compound, once the desired proportions have been attained in the catalyst system, the rhodium and iridium concentrations in the reaction medium may be maintained or adjusted by adding rhodium and/or iridium compounds.

In one particularly advantageous variant of the invention, when it proves necessary to add both rhodium and iridium in order to maintain and/or adjust the rhodium and iridium concentrations in the reaction medium, these two metal catalysts are introduced simultaneously in the form of a preprepared solution containing them. Such a technique has numerous advantages, especially that of simplifying the systems engineering and reducing the costs, since, by allowing rhodium and iridium to be added simultaneously, it obviates the need to prepare two separate catalyst solutions and introduce them separately into the reaction medium.

The catalyst solution may be prepared by any means which allows the simultaneous addition of rhodium and iridium in the form of a catalyst solution in which the rhodium and iridium are solubilized conjointly and simultaneously from the rhodium compounds and iridium compounds.

It is apparent from the Examples performed by the inventors of the present invention that the simultaneous solubilization of the rhodium and iridium, particularly in the form of rhodium iodide and iridium iodide, can be effected under conventional conditions of the type described in the Monsanto process for rhodium iodide alone.

In general terms, in both the modification phase and the stabilization phase of the catalyst system, the molar concentrations of rhodium and iridium are advantageously maintained in the reaction medium between 0.1 and 50 mmol/l for rhodium and between 0.1 and 25 mmol/l for iridium.

Furthermore, the iridium/rhodium atomic ratio is advantageously maintained at a value of between 1/99 and 99/1.

As explained previously, it is also possible to continue adding iridium compound in the modification phase until iridium is the only metal present in the homogeneous catalyst system.

The process of the invention is very particularly applicable to continuous processes for the manufacture of acetic acid and/or methyl acetate which are carried out in an installation comprising a reaction zone I, where the temperature is maintained at a value of between 150 and 250° C. and the total pressure is between $5.10^5$ Pa and $200.10^5$ Pa, and a flash zone II, where the product coming from the reaction zone I is partially vaporized at a pressure below that prevailing in the reaction zone I, the non-vaporized fraction coming from this flash zone II being recycled into the reaction zone I and the vaporized fraction being purified in a zone III, by separation/distillation/purification of the acetic acid and/or methyl acetate formed.

The various injections of iridium compounds, irrespective of their physical form, can be effected in different ways, as explained previously, but also at different locations of an installation of the type described above, comprising three main zones in particular.

In one variant, the iridium compounds, either solid or in solution, can be introduced directly into the reaction medium of the reaction zone I, into the non-vaporized fraction of the flash zone II or into the line for recycling said non-vaporized fraction from the zone II into the zone I, this last variant being preferred.

The iridium compounds can therefore be injected either directly into the reaction medium of zone I or into a stream recycled from the zone II or III into the reaction zone I.

As explained previously, the corrosion metals do not need to be removed, more than is customary, in order to perform the iridium additions.

The rules of the art of the conventional processes set a value of 5000 mg/kg (ppm) for the content of corrosion metals which is not to be exceeded in the reaction medium.

This rule may also be applied to the iridium additions and hence to the running of the carbonylation process throughout the modification phase, but also during the stabilization phase.

This concentration of corrosion metals can be kept at a value below or equal to 5000 mg/kg by any of the conventional means known to those skilled in the art which are already widely applied in processes catalyzed by rhodium alone or iridium alone:

selective precipitation,
liquid-liquid extraction,
passage over an ion exchange resin,
osmosis,
treatment on a selective membrane, etc.

As already explained previously, apart from the technical and practical advantages, the invention affords savings and cost improvements compared with the conventional method, which consists in stopping production to empty the installation, removing the reaction medium containing rhodium and replacing it with a different and specific reaction medium containing rhodium+iridium or iridium alone.

This makes it possible to avoid the production losses during the shutdown of the installation, the losses of rhodium or difficulties in recovering it, and the difficulties in restarting the installation which are associated with the fact that the new installation operating with a mixed catalyst system based on iridium and rhodium is run differently from the old installation operating with rhodium alone.

As explained previously, another particularly valuable advantage of the present invention is that it enables the water content of the reaction medium to be reduced below the conventional value of 14%, based on the weight of reaction medium, once the iridium additions have been effected.

This water content may even be reduced to values below 5% without detracting from the performance characteristics of the carbonylation process catalyzed by the rhodium+iridium mixture; this constitutes an additional advantage.

In fact, those skilled in the art are well aware that the carbonylation rate increases with the water content of the conventional reaction medium containing rhodium alone. The carbonylation rate reaches a maximum for water concentration values in the order of 14 to 15% (10 mol/l), as indicated in patent EP 0 055 618 and the publication by HJORTKJAER and JENSEN, Ind. Eng. Chem. Prod. Res. Dev., volume 16, no. 4, 1977, 281–285, and remains constant, even for water contents greater than 14 or 15%. The possibility afforded by the invention of reducing the water content in the case of a catalyst system based on rhodium and iridium, while maintaining the same carbonylation rates as those obtained with rhodium and a water content of 14%, affords an appreciable reduction in the energy costs of removing the water in the zone III for separation/distillation/purification of the acetic acid and/or methyl acetate produced.

An additional advantage of being able to lower the water content of the reaction medium, and particularly of being able to reduce it to a value below 5% by weight, based on the weight of said reaction medium, is that this makes it possible to envisage the complementary production of acetic acid and/or methyl acetate by means of a simultaneous methyl formate isomerization reaction under carbon monoxide pressure, in addition to the carbonylation of methanol. This makes it possible in particular to increase the production of acetic acid in an existing installation without requiring additional carbon monoxide, and to make substantial energy savings in the distillation steps.

Thus, as soon as the value of the water concentration in the reaction medium has dropped to a value below or equal to 5% by weight, based on the weight of reaction medium, it will be possible easily to introduce methyl formate into the reaction medium and simultaneously to carry out the carbonylation reaction of methanol or carbonylatable derivative and the methyl formate isomerization reaction under carbon monoxide pressure, as is apparent from international patent application WO 97/35828.

It will even be possible under these conditions gradually to stop the introduction of methanol or carbonylatable derivative of methanol into the reaction medium in order to change to a system operating only with methyl formate isomerization under carbon monoxide pressure (as is apparent from international patent application WO 97/35829).

Finally, it has become apparent that when the catalyst system initially based on rhodium has been modified according to the present invention, i.e. converted under particularly smooth conditions to a catalyst system based on a mixture of rhodium and iridium, or even a catalyst system consisting exclusively of iridium, it is also possible to modify this catalyst system for the gradual introduction of a platinum compound so as to change gradually to a process for the manufacture of acetic acid and/or methyl acetate in the presence of a homogeneous catalyst comprising proportions of iridium and platinum, affording the advantages described in patent application WO 00/27785. In such a case, the platinum concentration is advantageously kept at a value of between 1 mmole and 25 mmole per liter of reaction medium.

EXAMPLES

Series of experiments were performed on synthetic solutions (reconstituted carbonylation reaction medium) and on an actual industrial carbonylation reaction medium (50 ml samples taken directly from the carbonylation reactor of the reaction zone I) which were in every respect identical between successive series except for the composition of the catalyst system and/or the concentration of corrosion metals and/or the water concentration.

Unless otherwise stated, the quantities of catalysts (Rh or Ir) are designated by [Rh] or [Ir] and expressed in millimoles (mmol).

The results of these different series of experiments are given for each experiment as the carbonylation rate calculated on the basis of the CO consumption measured after a reaction time of 10 minutes (Rcarb 10'), which corresponds to the amount of acetyl radicals formed (acetic acid+methyl acetate). Rcarb is expressed in mol/liter of final reaction medium per hour=mol/(l.h).

The stability of the catalyst system is assessed by observation of the final reaction mixture—after cooling to room temperature and degassing to atmospheric pressure—for the presence or absence of metal deposit or metal black.

1. Standard Procedures 1.1 Procedure for the Synthetic Solutions
Preparation of the Catalyst Solution
Rhodium iodide, iridium iodide, corrosion metals, 9 g of pure acetic acid and 3 g of water are introduced into a 100 ml Hastelloy® B2 autoclave. The autoclave is placed under a CO pressure of 5 bar absolute at room temperature. The temperature is raised to 190° C., which takes about 1 hour, and the mixture is left to stand for 10 minutes at 190° C. under autogenous pressure (10 bar).

Carbonylation Reaction (Carried Out Immediately Afterwards)

From a reservoir located above the autoclave, a mixture made up of water, methyl iodide, methyl acetate, acetic acid and methanol is injected under CO pressure. The composition of the synthetic reaction medium, excluding methanol, is as follows: water 14%, methyl iodide 9%, methyl acetate 2%, rhodium, iridium and corrosion metals variable from experiment to experiment, acetic acid qsp 100%. The weight of the synthetic reaction medium, excluding methanol, is about 56–57 g and the added methanol represents 10% of this weight, i.e. 5.6 g.

The temperature is raised to 190° C. again and the carbonylation reaction is carried out with the injection of CO under 30 bar absolute at 190±0.5° C. for 10 minutes. The autoclave is cooled and emptied and the presence or absence of metal deposit is noted.

Expression of the Data in the Tables

The concentrations of catalysts, Rh and Ir, are expressed in millimoles of the appropriate metal in the experimental reaction medium.

The corrosion metals [CorMet] are introduced in the form of metal iodide or metal carbonyl; the total concentration is expressed in mg/kg (ppm), based on the weight of reaction medium excluding methanol (56–57 g). The distribution by weight of the corrosion metals is as follows:

Iron: 20%; nickel: 30%; chromium: 20%; molybdenum: 30%.

1.2 Procedure for the Industrial Reaction Medium
Preparation of the Carbonylation Reaction Medium
50 ml samples are taken in leaktight bottles at an analytical sampling point on an industrial reactor for the carbonylation of methanol under catalysis with rhodium alone, and are kept in the dark at room temperature. The analytical sampling point is located on the line joining the reactor—zone I—to the flash zone—zone II—near the reactor (the sample being taken under leaktight conditions by means of a DOPAK® system). 50 ml of industrial reaction medium are introduced into a 100 ml Hastelloy® B2 autoclave (i.e. about 56–57 g).

The industrial reaction medium has the following composition: water 14%, methyl iodide 9%, methyl acetate 2%, rhodium 600 mg/kg, corrosion metals (naturally present in the industrial reaction medium due to corrosion of the materials constituting the industrial equipment) 5000 mg/kg (iron 1000, nickel 1500, chromium 1000, molybdenum 1500 mg/kg), acetic acid qsp 100%. The introduction of iridium iodide varies from experiment to experiment.

The autoclave is closed and placed under a CO pressure of 5 bar absolute at room temperature.

The mixture is heated to 190° C. under autogenous pressure (10 bar), which takes about 1 h, and is left to stand for 10 minutes at 190° C. About 5.6 g of methanol (i.e. about 10% of the reaction mixture) are then added from the reservoir under CO pressure. The mixture is heated to 190° C. and the carbonylation reaction is carried out with CO injection under 30 bar absolute at 190±0.5° C. for 10 minutes. The autoclave is cooled and emptied and the presence or absence of metal deposit is noted.

Expression of the Data in the Tables (cf. 1.1 Above)

2. Experiments With Synthetic Solutions 2.1 Zero Concentration of Corrosion Metals These experiments are performed by applying the standard procedure given in 1.1.

They are performed in the absence of corrosion metals ([CorMet]=0) and are considered as comparative experiments to be used for reference purposes in the following experiments where [CorMet]>0. Nevertheless, these experiments show the influence of increasing additions of iridium from 0 to 0.8 millimole for a constant rhodium concentration of 0.33–0.34 millimole. The carbonylation rate, which is constant at 5–6 mol/l.h for Rh/Ir molar ratios of 100/0 to 70/30, then increases to 7.5 and 10 mol/l.h for Rh/Ir molar ratios of 50/50 and 30/70.

The experiments in the presence of Rh+Ir show a very good stability of the catalyst system—absence of metal deposit—in contrast to those performed with Rh alone.

The conditions and results are collated in attached Table 1.

2.2 Concentrations of Corrosion Metals from 0 to 4000 mg/kg

These experiments are performed according to the standard procedure given in 1.1.

For each Rh/Ir molar ratio of between 100/0 and 30/70, the concentration of corrosion metals is studied over the range 0–4000 mg/kg.

All the conditions and results of the various experiments performed are collated in attached Table 2.

All the experiments performed with [CorMet]=0 are comparative experiments.

2.2.1 Experiments with [Rh]=Constant; [Ir]=Variable

Rh/Ir molar ratio=100/0; [Rh]=0.33 to 0.34 mmol; [Ir]=0

Comparative experiments outside the invention, because [Ir]=0, used for reference purposes Rh/Ir molar ratio=90/10; [Rh]=0.33 to 0.34 mmol; [Ir] ≅0.04 mmol Rh/Ir molar ratio=80/20; [Rh]=0.33 to 0.34 mmol; [Ir] ≅0.08–0.09 mmol Rh/Ir molar ratio=70/30; [Rh]=0.33 to 0.34 mmol; [Ir] ≅0.14 mmol Rh/Ir molar ratio=50/50; [Rh]=0.33 to 0.34 mmol; [Ir] ≅0.33 mmol Rh/Ir molar ratio=30/70; [Rh]=0.33 to 0.34 mmol; [Ir] ≅0.8 mmol The following conclusions can be drawn from all these experiments:

⇒For Rh/Ir molar ratios of between 90/10 and 50/50 (exclusive), the carbonylation rate of the system comprising Rh+Ir is maintained relative to that of the system comprising Rh alone (Rh/Ir=100/0), irrespective of the concentrations of corrosion metals between 0 and 4000 mg/kg (between 5 and 6 mol/l.h).

⇒For Rh/Ir molar ratios of 50/50 to 30/70, the carbonylation rate of the system comprising Rh+Ir decreases as the concentration of corrosion metals increases from 0 to 4000 mg/kg (from 7.5 to 5.5 mol/l.h for Rh/Ir=50/50 and from 10 to 8 mol/l.h for Rh/Ir=30/70).

⇒Stability of the catalyst system:

For the experiments with rhodium alone, a metal deposit is present except for a concentration of corrosion metals of 4000 mg/kg.

For all the other experiments performed in the presence of Rh+Ir, a metal deposit is absent, irrespective of the concentration of corrosion metals.

2.2.2 Experiments with [Rh]+[Ir]=constant=0.33–0.34 mmol

Rh/Ir molar ratio=100/0; [Rh]=0.33–0.34 is again a reference series of comparative experiments because [Ir]=0

Rh/Ir molar ratio=70/30; [Rh]≅0.23 mmol; [Ir]≅0.11 mmol

Rh/Ir molar ratio=50/50; [Rh]≅0.165 mmol; [Ir]≅0.166 mmol

Rh/Ir molar ratio=30/70; [Rh]≅0.10 mmol; [Ir]≅0.23 mmol

The following observations are made:

⇒For Rh/Ir molar ratios of between 70/30 and 50/50 (inclusive), the carbonylation rate of the system comprising Rh+Ir is only slightly reduced, if at all, by increasing the concentration of corrosion metals from 0 to 4000 mg/kg (or at least is not reduced by more than in the reference experiments with Rh/Ir=100/0).

This slight reduction in carbonylation rate as [CorMet] changes from 0 to 4000 mg/kg is estimated to be 5% for Rh/Ir=100/0, 12% for 70/30, 0% for 50/50 and 33% in the experiments with Rh/Ir=30/70.

⇒Stability of the catalyst system:

Same observations as in paragraph 2.2.1.

3. Experiments with an Industrial Reaction Medium

These experiments are performed by applying the standard procedure given in 1.2.

Optimization of the amount of methanol introduced

In this series of comparative experiments (absence of iridium), the amount of added methanol (10% of the reaction medium in the standard procedure) was varied between 5 and 15%. All the other parameters are identical, particularly [Rh]=0.33–0.34 mmol, [CorMet]=5000 mg/kg and [Water]=14%. The maximum carbonylation rate of 7 moles/l.h is obtained for 10% of added methanol; it decreases very slightly when the amount of added methanol increases to 12 or 15% (6 mol/l.h).

The conditions and results of these experiments are recorded in Table 3-1.

3.2 Experiments with [Rh]=constant: [Ir]=Variable

In this series of experiments, the results and conditions of which are collated in Table 3-2 below, increasing amounts of iridium were added to an initial industrial reaction medium of constant composition, particularly [Water]=14%, [CorMet]=5000 mg/kg and [Rh]=0.33–0.34 mmol.

The Rh/Ir molar ratios are adjusted by adding increasing amounts of iridium:

Rh/Ir=100/0: comparative experiments (absence of iridium)

Rh/Ir=90/10, 80/20, 70/30, 50/50 and 30/70: experiments according to the invention Note 1: Experiments with the same Rh/Ir ratio are generally duplicated.

Note 2: In Experiment 602 (Rh/Ir=30/70), the 10% of added methanol is replaced with 25% of methyl acetate; no influence on Rcarb is observed.

⇒Increasing amounts of iridium can be added to an actual industrial reaction medium (conventional, catalysis with rhodium alone) without loss of production or loss of stability of the catalyst system.

The carbonylation rate for Rh alone (6 to 7 mol/l.h) is maintained up to an Rh/Ir molar ratio of 50/50 or improved for Rh/Ir=30/70 (Rcarb=8–8.5 mol/l.h).

No metal deposit is observed, irrespective of the Rh/Ir molar ratios between 100/0 and 30/70.

3.3 Influence of the Water Concentration and the Rh/Ir Ratio

The following variant of standard procedure 1.2 is applied:

For the experiments in which it is necessary, the water concentration is adjusted to x % (x=12%, 10%, 8% or 6%) by introducing an amount of acetic anhydride calculated on the basis of the initial water concentration of 14% (14−x %) and the initial sample of industrial reaction medium of 50 ml; this amount of acetic anhydride is introduced into the 50 ml of reaction medium right at the start of the experiment, before closure of the autoclave and the application of a carbon monoxide pressure of 5 bar. The standard procedure is then followed.

In these 4 series of experiments, the initial composition of the reaction medium, in which [CorMet]=5000 mg/kg, and in practical terms the catalyst concentration [Rh]+[Ir]=0.33 to 0.44 millimole, are kept constant. (It should be pointed out that in the 4th series—Experiments 734 to 739—the amount of reaction medium is reduced to 43 ml/48 g, so the added methanol is 4.8 g.)

The conditions and results of the experiments are collated in attached Table 3-3.

Rh/Ir molar ratio=100/0; [Rh]=0.33–0.34 mmol; [Ir]=0

Comparative experiments outside the invention, because [Ir]=0, used for reference purposes Rh/Ir molar ratio=90/10; [Rh]=0.33–0.34 mmol; [Ir]≅0.04 mmol Rh/Ir molar ratio=80/20; [Rh]=0.35–0.36 mmol; [Ir]≅0.09 mmol Rh/Ir molar ratio=70/30; [Rh]=0.23–0.24 mmol; [Ir]≅0.10 mmol i.e. [Rh]+[Ir]=0.33–0.44 mmol.

These various experiments are directly comparable because the [Rh]+[Ir] values are constant in practical terms, particularly for the series in which Rh/Ir=100/0 and 70/30, where the [Rh]+[Ir] values are identical at 0.33–0.34 mmol.

The following overall conclusions can be drawn:

⇒A decrease in water content results in a decrease in carbonylation rate for each series, irrespective of the Rh/Ir molar ratios between 100/0 and 70/30.

⇒In practical terms, for each water concentration, the carbonylation rates increase in the following order:

Rh/Ir=100/0 ≦ Rh/Ir=90/10 ≦ Rh/Ir=80/20 ≦ Rh/Ir=70/30

⇒The reduction in water concentration from 14% to 12% or 10% is accompanied by only a very small decrease in the carbonylation rate: Rcarb (Rh/Ir=70/30, water=12%)=Rcarb (Rh/Ir=100/0, water=14%).

⇒There is no visible (negative) influence of the presence of 5000 mg/kg of corrosion metals on the increasing additions of iridium, either in terms of carbonylation rate or in terms of stability of the catalyst system comprising Rh+Ir (absence of metal deposit).

4. Simultaneous Solubilization of Rhodium and Iridium

These Examples describe the simultaneous solubilization of rhodium and iridium—in the forms of rhodium iodide and iridium iodide—under conditions derived from the conventional conditions of the type described in the MONSANTO process for rhodium iodide alone. The resulting solutions are catalyst solutions which are suitable for effecting simultaneous additions of these two catalysts—Rh and Ir—to the carbonylation reaction medium.

Rhodium iodide, iridium iodide, water and acetic acid are introduced into a 100 ml Hastelloy® B2 autoclave in the amounts indicated in Table 4-1, which shows the operating conditions. The autoclave is placed under CO pressure at room temperature and heated to 110° C., the pressure is adjusted to and maintained at $5.10^5$ Pascal (5 bar) with CO and the reaction is continued at 110° C. for 5 or 8 hours, depending on the particular experiment.

The autoclave is cooled and the catalyst solution is collected and weighed in order to verify the absence of leaks and thereby validate the experiment.

The catalyst solution is analyzed for appearance, presence or absence of deposit, and rhodium and iridium concentrations by atomic absorption spectrometry.

The autoclave is also inspected in order to verify the presence or absence of metal deposit. These various analytical results are given in Table 4-2.

The clear appearance of the catalyst solutions, together with a comparison of the theoretical concentrations and the concentrations determined by analysis of the final solution, prove that the rhodium and iridium have been totally solubilized.

It is therefore possible to prepare concentrated catalyst solutions—950 mg Rh/kg solution and 950 to 2600 mg Ir/kg solution (Experiments 780, 787 and 785)—or very concentrated catalyst solutions—1% by weight of Rh and 1.4% by weight of Ir (Experiment 788).

TABLE 1

EXPERIMENTS WITH SYNTHETIC SOLUTIONS
ZERO CONCENTRATION OF CORROSION METALS

| Experiment n° | Type of experiment | Metal deposit | CorMet mg/kg | Rh mmol | Ir mmol | Rh mol % | Ir mol % | Rcarb 10' mol/l · h |
|---|---|---|---|---|---|---|---|---|
| 606 | Comparative | Present | 0 | 0.334 | 0 | 100 | 0 | 5.5 |
| 719 | Comparative | Present | 0 | 0.337 | 0 | 100 | 0 | 4.5 |
| 610 | Comparative | Absent | 0 | 0.333 | 0.037 | 90 | 10 | 5.3 |
| 611 | Comparative | Absent | 0 | 0.336 | 0.084 | 80 | 20 | 6 |
| 721 | Comparative | Absent | 0 | 0.334 | 0.145 | 70 | 30 | 5 |
| 726 | Comparative | Absent | 0 | 0.334 | 0.332 | 50 | 50 | 7.5 |
| 730 | Comparative | Absent | 0 | 0.333 | 0.777 | 30 | 70 | 10.5 |
| 599 | Comparative | Absent | 0 | 0.334 | 0.801 | 30 | 70 | 10 |

TABLE 2

EXPERIMENTS WITH SYNTHETIC SOLUTIONS
CONCENTRATION OF CORROSION METALS from 0 to 4000 mg/kg

| Experiment n° | Type of experiment | Metal deposit | CorMet mg/kg | Rh mmol | Ir mmol | Rh mol % | Ir mol % | Rcarb 10' Ir/Rh = 0/100 |
|---|---|---|---|---|---|---|---|---|
| 606 | Comparative | Present | 0 | 0.334 | 0 | 100 | 0 | 5.5 |
| 719 | Comparative | Present | 0 | 0.337 | 0 | 100 | 0 | 4.5 |
| 715 | Comparative | Present | 100 | 0.335 | 0 | 100 | 0 | 6 |
| 716 | Comparative | Present | 1000 | 0.333 | 0 | 100 | 0 | 5 |
| 717 | Comparative | Present | 2000 | 0.333 | 0 | 100 | 0 | 5 |
| 720 | Comparative | Absent | 4000 | 0.335 | 0 | 100 | 0 | 5 |

| Experiment n° | Type of experiment | Metal deposit | CorMet mg/kg | Rh mmol | Ir mmol | Rh mol % | Ir mol % | Rcarb 10' Ir/Rh = 10/90 |
|---|---|---|---|---|---|---|---|---|
| 610 | Comparative | Absent | 0 | 0.333 | 0.037 | 90 | 10 | 5.3 |
| 612 | Acc. to invention | Absent | 100 | 0.336 | 0.037 | 90 | 10 | 5 |
| 613 | Acc. to invention | Absent | 1000 | 0.334 | 0.037 | 90 | 10 | 6 |
| 614 | Acc. to invention | Absent | 2000 | 0.333 | 0.037 | 90 | 10 | 5.3 |
| 615 | Acc. to invention | Absent | 4000 | 0.335 | 0.042 | 90 | 10 | 5.3 |

| Experiment n° | Type of experiment | Metal deposit | CorMet mg/kg | Rh mmol | Ir mmol | Rh mol % | Ir mol % | Rcarb 10' Ir/Rh = 20/80 |
|---|---|---|---|---|---|---|---|---|
| 611 | Comparative | Absent | 0 | 0.336 | 0.084 | 80 | 20 | 6 |
| 616 | Acc. to invention | Absent | 100 | 0.335 | 0.083 | 80 | 20 | 6 |
| 617 | Acc. to invention | Absent | 1000 | 0.335 | 0.089 | 80 | 20 | 6 |
| 618 | Acc. to invention | Absent | 2000 | 0.334 | 0.085 | 80 | 20 | 5.5 |
| 622 | Acc. to invention | Absent | 4000 | 0.334 | 0.083 | 80 | 20 | 6 |

| Experiment n° | Type of experiment | Metal deposit | CorMet mg/kg | Rh mmol | Ir mmol | Rh mol % | Ir mol % | Rcarb 10' Ir/Rh = 30/70 |
|---|---|---|---|---|---|---|---|---|
| 721 | Comparative | Absent | 0 | 0.334 | 0.145 | 70 | 30 | 5 |
| 722 | Acc. to invention | Absent | 100 | 0.335 | 0.143 | 70 | 30 | 6 |
| 723 | Acc. to invention | Absent | 4000 | 0.333 | 0.144 | 70 | 30 | 5.5 |
| 724 | Comparative | Absent | 0 | 0.235 | 0.108 | 70 | 30 | 4 |
| 725 | Acc. to invention | Absent | 4000 | 0.233 | 0.107 | 70 | 30 | 3.5 |

| Experiment n° | Type of experiment | Metal deposit | CorMet mg/kg | Rh mmol | Ir mmol | Rh mol % | Ir mol % | Rcarb 10' Ir/Rh = 50/50 |
|---|---|---|---|---|---|---|---|---|
| 726 | Comparative | Absent | 0 | 0.334 | 0.332 | 50 | 50 | 7.5 |
| 727 | Acc. to invention | Absent | 4000 | 0.333 | 0.334 | 50 | 50 | 5.5 |
| 728 | Comparative | Absent | 0 | 0.165 | 0.166 | 50 | 50 | 3 |
| 729 | Acc. to invention | Absent | 4000 | 0.165 | 0.166 | 50 | 50 | 3 |

| Experiment n° | Type of experiment | Metal deposit | CorMet mg/kg | Rh mmol | Ir mmol | Rh mol % | Ir mol % | Rcarb 10' Ir/Rh = 70/30 |
|---|---|---|---|---|---|---|---|---|
| 599 | Comparative | Absent | 0 | 0.334 | 0.801 | 30 | 70 | 10 |
| 730 | Comparative | Absent | 0 | 0.333 | 0.777 | 30 | 70 | 10.5 |
| 731 | Acc. to invention | Absent | 4000 | 0.333 | 0.777 | 30 | 70 | 8 |
| 732 | Comparative | Absent | 0 | 0.099 | 0.233 | 30 | 70 | 3 |
| 733 | Acc. to invention | Absent | 4000 | 0.103 | 0.233 | 30 | 70 | 2 |

The carbonylation rates are expressed in mol per liter per hour = mol/l · h

TABLE 3-1

EXPERIMENTS WITH AN INDUSTRIAL REACTION MEDIUM
OPTIMIZATION OF THE AMOUNT OF METHANOL INTRODUCED

| Experiment n° | Type of experiment | MeOH % | CorMet mg/kg | Rh mmol | Ir mmol | Rh mol % | Ir mol % | Rcarb 10' mol/l · h |
|---|---|---|---|---|---|---|---|---|
| 583 | Comparative | 5 | 5000 | 0.336 | 0 | 100 | 0 | 2 |
| 581 | Comparative | 10 | 5000 | 0.329 | 0 | 100 | 0 | 7 |
| 604 | Comparative | 12 | 5000 | 0.329 | 0 | 100 | 0 | 6.4 |
| 605 | Comparative | 15 | 5000 | 0.327 | 0 | 100 | 0 | 6 |

TABLE 3-2

EXPERIMENTS WITH AN INDUSTRIAL REACTION MEDIUM
EXPERIMENTS WITH [Rh] = CONSTANT; [Ir] = VARIABLE

| Experiment n° | Type of experiment | Metal deposit | CorMet mg/kg | Rh mmol | Ir mmol | Rh mol % | Ir mol % | Rcarb 10' mol/l · h |
|---|---|---|---|---|---|---|---|---|
| 581 | Comparative | Absent | 5000 | 0.329 | 0 | 100 | 0 | 7 |
| 603 | Comparative | Absent | 5000 | 0.341 | 0 | 100 | 0 | 7 |
| 655 | Comparative | Absent | 5000 | 0.329 | 0 | 100 | 0 | 6.5 |
| 656 | Acc. to invention | Absent | 5000 | 0.338 | 0.037 | 90 | 10 | 7 |
| 661 | Acc. to invention | Absent | 5000 | 0.332 | 0.038 | 90 | 10 | 6.5 |
| 657 | Acc. to invention | Absent | 5000 | 0.338 | 0.085 | 80 | 20 | 6.5 |
| 662 | Acc. to invention | Absent | 5000 | 0.333 | 0.083 | 80 | 20 | 6 |
| 664 | Acc. to invention | Absent | 5000 | 0.331 | 0.143 | 70 | 30 | 6.5 |
| 663 | Acc. to invention | Absent | 5000 | 0.339 | 0.144 | 70 | 30 | 7 |
| 659 | Acc. to invention | Absent | 5000 | 0.338 | 0.336 | 50 | 50 | 7 |
| 660 | Acc. to invention | Absent | 5000 | 0.335 | 0.782 | 30 | 70 | 8.5 |
| 602 (25% AcOMe) | Acc. to invention | Absent | 5000 | 0.333 | 0.774 | 30 | 70 | 8 |

TABLE 3-3

EXPERIMENTS WITH AN INDUSTRIAL REACTION MEDIUM
INFLUENCE OF THE WATER CONCENTRATION AND THE Rh/Ir RATIO

| Experiment n° | Type of experiment | Metal deposit | Water % | Rh mmol | Ir mmol | Rh mol % | Ir mol % | Rcarb 10' mol/l · h |
|---|---|---|---|---|---|---|---|---|
| 700 | Comparative | Absent | 14 | 0.338 | 0 | 100 | 0 | 7 |
| 699 | Comparative | Absent | 12 | 0.339 | 0 | 100 | 0 | 6 |
| 698 | Comparative | Absent | 10 | 0.332 | 0 | 100 | 0 | 4.5 |
| 696 | Comparative | Absent | 8 | 0.335 | 0 | 100 | 0 | 4 |
| 697 | Comparative | Absent | 6 | 0.342 | 0 | 100 | 0 | 3 |
| 701 | Acc. to invention | Absent | 14 | 0.332 | 0.038 | 90 | 10 | 7 |
| 702 | Acc. to invention | Absent | 12 | 0.343 | 0.038 | 90 | 10 | 6 |
| 706 | Acc. to invention | Absent | 10 | 0.331 | 0.039 | 90 | 10 | 5 |
| 704 | Acc. to invention | Absent | 8 | 0.343 | 0.038 | 90 | 10 | 4.3 |
| 705 | Acc. to invention | Absent | 6 | 0.335 | 0.038 | 90 | 10 | 3.2 |
| 707 | Acc. to invention | Absent | 14 | 0.355 | 0.088 | 80 | 20 | 6.5 |
| 708 | Acc. to invention | Absent | 12 | 0.346 | 0.088 | 80 | 20 | 6 |
| 709 | Acc. to invention | Absent | 10 | 0.352 | 0.086 | 80 | 20 | 5 |
| 710 | Acc. to invention | Absent | 8 | 0.353 | 0.088 | 80 | 20 | 4 |
| 711 | Acc. to invention | Absent | 6 | 0.360 | 0.086 | 80 | 20 | 4 |
| 734 | Acc. to invention | Absent | 14 | 0.233 | 0.100 | 70 | 30 | 7.5 |
| 738 | Acc. to invention | Absent | 12 | 0.235 | 0.100 | 70 | 30 | 7 |
| 736 | Acc. to invention | Absent | 10 | 0.233 | 0.102 | 70 | 30 | 5.6 |
| 737 | Acc. to invention | Absent | 8 | 0.233 | 0.101 | 70 | 30 | 4.3 |
| 739 | Acc. to invention | Absent | 6 | 0.233 | 0.101 | 70 | 30 | 4 |

TABLE 4-1

SIMULTANEOUS SOLUBILIZATION OF RHODIUM AND IRIDIUM
TABLE OF OPERATING CONDITIONS

| Exp. N° | Water g | Acetic acid g | Iridium iodide g | Rhodium iodide g | Reaction time hours | CO pressure bar | Temperature ° C. |
|---|---|---|---|---|---|---|---|
| 780 | 15.74 | 58.04 | 0.228 | 0.329 | 5 | 5 | 110 |
| 787 | 15.74 | 58.04 | 0.423 | 0.332 | 5 | 5 | 110 |
| 785 | 15.74 | 58.04 | 0.639 | 0.329 | 5 | 5 | 110 |
| 788 | 9.00 | 28.22 | 2.000 | 2.000 | 8 | 5 | 110 |

TABLE 4-2

SIMULTANEOUS SOLUBILIZATION OF RHODIUM AND IRIDIUM
TABLE OF RESULTS

| Exp. N° | Theoretical iridium mg/kg | Iridium determined mg/kg | Theoretical rhodium mg/kg | Rhodium determined mg/kg | Appearance of solution after reaction |
|---|---|---|---|---|---|
| 780 | 941 | 875 | 942 | 917 | Clear yellow-brown solution Absence of autoclave deposit |
| 787 | 1742 | 1680 | 948 | 845 | Clear yellow-brown solution Absence of autoclave deposit |

TABLE 4-2-continued

SIMULTANEOUS SOLUBILIZATION OF RHODIUM AND IRIDIUM
TABLE OF RESULTS

| Exp. N° | Theoretical iridium mg/kg | Iridium determined mg/kg | Theoretical rhodium mg/kg | Rhodium determined mg/kg | Appearance of solution after reaction |
|---|---|---|---|---|---|
| 785 | 2624 | 2560 | 937 | 871 | Clear yellow-brown solution Absence of autoclave deposit |
| 788 | 14892 | 14040 | 10324 | 9421 | Clear yellow-brown solution Absence of autoclave deposit |

What is claimed is:

1. In a process for continuous manufacture of acetic acid and/or methyl acetate by carbonylation of methanol or a carbonylatable derivative of methanol into acetic acid and/or methyl acetate in a homogeneous liquid phase and under carbon monoxide pressure, in the presence of a homogeneous catalyst system comprising a rhodium-based homogeneous catalyst and a halogenated promoter, and in the presence of at least 14% by weight water, said continuous process being carried out in a plant comprising a reaction zone I, with a temperature maintained at a value between 150 and 250° C. a total pressure between $5.10^5$ Pa and $200.10^5$ Pa, and a flash zone II, where the product from the reaction zone I is partially vaporized at a pressure below the pressure in the reaction zone I, the non-vaporized fraction from this flash zone II being recycled into the reaction zone I and the vaporized fraction being purified in a zone III by separation/distillation/purification of the acetic acid and/or methyl acetate formed, the improvement comprising: adding an iridium compound to the catalyst system gradually over time, in order to gradually modify the composition of the homogeneous catalyst system, to obtain a catalyst system containing a predetermined atomic ratio of rhodium to iridium, thereby modifying the catalyst composition without stopping the process, and continuing the continuous manufacture of acetic acid and/or methyl acetate, while maintaining the catalyst system containing said predetermined atomic ratio by adding a rhodium compound, an iridium compound or both a rhodium and an iridium compound.

2. Process according to claim 1, wherein concentrations of rhodium and iridium in the reaction medium are maintained by simultaneously adding rhodium and iridium by means of a catalyst solution containing rhodium and iridium in solution.

3. Process according to claim 1, wherein said adding of iridium compound is effected by adding the compound in the form of presolubilized iridium.

4. Process according to claim 3, wherein the iridium compound is presolubilized by a process compatible with solubilizing the rhodium-based catalyst.

5. Process according to claim 1, wherein said addition of iridium compound is effected in the form of a solid iridium derivative which is solubilized in situ in the reaction medium.

6. Process according to claim 1, wherein said addition of iridium compound is effected continuously or batchwise.

7. Process according to claim 1, wherein the rhodium and iridium are maintained in the reaction medium in concentrations between 0.1 and 50 mmol/l and between 0.1 and 25 mmol/l, respectively.

8. Process according to claim 7, wherein said addition of iridium compound is effected so as to compensate losses of rhodium, the lost rhodium being replaced with iridium, thereby maintaining a constant total concentration of catalytic metals.

9. Process according to claim 1, wherein said predetermined atomic ratio of rhodium to iridium is between 1/99 and 99/1.

10. Process according to claim 1, wherein said addition of iridium compound is effected until iridium is the only metal present in the homogeneous catalyst system, said predetermined atomic ratio of rhodium to iridium being 0/100.

11. Process according to claim 1, wherein the addition of said iridium compound is effected by injection into the reaction medium of the reaction zone I.

12. Process according to claim 1, wherein the addition of iridium compound is effected by injection into a stream recycled from the zone II or III into the reaction zone I.

13. Process according to claim 1, wherein corrosion metals in the reaction medium are monitored in order to maintain a concentration below or equal to 5000 mg/kg.

14. Process according to claim 1, further comprising a step of reducing water content of the reaction medium to a value below 14% by weight, based on the weight of reaction medium.

15. Process according to claim 13, wherein the concentration of water in the reaction medium is maintained at a value below 5% by weight, based on the weight of reaction medium.

16. Process according to claim 15, wherein methyl formate is introduced into the reaction medium during said further step and wherein the carbonylation reaction of methanol or carbonylatable derivative of methanol and a methyl formate isomerization reaction are carried out simulatenously under carbon monoxide pressure.

17. Process according to claim 16, wherein the introduction of methanol or carbonylatable derivative of methanol into the reaction medium is stopped gradually in order to change to a system operating only with methyl formate isomerization under carbon monoxide pressure.

18. Process according to claim 1, further comprising a step for gradual modification of the composition of the homogeneous catalyst by adding a platinum compound over time, the platinum compound being maintained at a value of between 1 mmole and 25 mmol per liter of reaction medium.

* * * * *

UNITED STATES PATENT AND TRADEMARK OFFICE
CERTIFICATE OF CORRECTION

PATENT NO. : 7,009,070 B2 Page 1 of 1
APPLICATION NO. : 10/433474
DATED : March 7, 2006
INVENTOR(S) : Daniel Thiebaut et al.

It is certified that error appears in the above-identified patent and that said Letters Patent is hereby corrected as shown below:

Column 20, line 43, change "13" to --14--.

Signed and Sealed this

Fifth Day of February, 2008

JON W. DUDAS
*Director of the United States Patent and Trademark Office*